United States Patent
Conrad et al.

(10) Patent No.: US 12,088,137 B2
(45) Date of Patent: Sep. 10, 2024

(54) MEDICAL DEVICE WITH POWER-UP ROUTINE

(71) Applicants: Roche Diabetes Care, Inc., Indianapolis, IN (US); Roche Diabetes Care, Inc., Indianapolis, IN (US)

(72) Inventors: Klaus Conrad, Mannheim (DE); Walter Fieber, Absteinbach (DE)

(73) Assignee: Roche Diabetes Care, Inc., Indianapolis, IN (US)

(*) Notice: Subject to any disclaimer, the term of this patent is extended or adjusted under 35 U.S.C. 154(b) by 702 days.

(21) Appl. No.: 17/334,046

(22) Filed: May 28, 2021

(65) Prior Publication Data
US 2021/0288515 A1 Sep. 16, 2021

Related U.S. Application Data

(63) Continuation of application No. PCT/EP2019/082796, filed on Nov. 27, 2019.

(30) Foreign Application Priority Data

Nov. 30, 2018 (EP) .................................... 18209404

(51) Int. Cl.
*G01R 31/385* (2019.01)
*A61M 5/142* (2006.01)
*H02J 7/00* (2006.01)

(52) U.S. Cl.
CPC ... *H02J 7/007184* (2020.01); *A61M 5/14244* (2013.01); *H02J 7/0047* (2013.01); *A61M 2205/18* (2013.01); *A61M 2205/8206* (2013.01)

(58) Field of Classification Search
CPC ............. H02J 7/007184; H02J 7/0047; A61M 2205/18

(Continued)

(56) References Cited

U.S. PATENT DOCUMENTS 4,488,555 A 12/1984 Imran
4,685,903 A 8/1987 Cable et al.
(Continued)

FOREIGN PATENT DOCUMENTS

CN 1083595 A 3/1994
CN 202929116 U 5/2013
(Continued)

OTHER PUBLICATIONS

International Search Report and Written Opinion of the International Searching Authority, PCT/EP2019/082796, Feb. 12, 2020, 15 pages.

(Continued)

*Primary Examiner* — Nathaniel R Pelton
(74) *Attorney, Agent, or Firm* — Bose McKinney & Evans LLP

(57) ABSTRACT

The present disclosure relates to a method for powering up a medical device powered by a battery. The method includes executing an initial battery test. In the initial battery test, a difference voltage between a battery voltage measured without and with a test load is determined. The test load is favorably dimensioned not to significantly stress the battery. The difference voltage is compared with a difference voltage threshold, the difference voltage threshold being predefined in dependence of the no-test-load voltage. The method further includes providing an alarm if the difference voltage is above the difference voltage threshold. The present disclosure further concerns a medical device that implements the method and a method for determining the relation between the difference voltage and the difference voltage threshold. The disclosure can be used to ensure that an alarm is provided if a newly inserted battery is too weak to power the medical device.

14 Claims, 2 Drawing Sheets

(58) Field of Classification Search
USPC .......................................................... 324/426
See application file for complete search history.

(56) References Cited

U.S. PATENT DOCUMENTS

| | | | |
|---|---|---|---|
| 4,830,866 | A | 5/1989 | Manser et al. |
| 5,381,350 | A | 1/1995 | Fiorina et al. |
| 5,717,315 | A | 2/1998 | Maeno et al. |
| 6,005,369 | A | 12/1999 | Rogers |
| 7,239,146 | B2 | 7/2007 | James et al. |
| 2003/0088376 | A1 | 5/2003 | Zimmerman et al. |
| 2008/0262560 | A1 | 10/2008 | Eriksson |
| 2009/0273349 | A1 | 11/2009 | Rondoni et al. |
| 2010/0201368 | A1 | 8/2010 | Doerr et al. |
| 2011/0040247 | A1 | 2/2011 | Mandro et al. |
| 2011/0279123 | A1* | 11/2011 | Rufer ................. A61M 5/14276 324/427 |
| 2013/0147490 | A1* | 6/2013 | Lindegger ........... A61M 5/1413 324/435 |
| 2015/0105842 | A1 | 4/2015 | Lamont et al. |
| 2015/0168501 | A1 | 6/2015 | Simeth |
| 2016/0067510 | A1 | 3/2016 | Norton et al. |

FOREIGN PATENT DOCUMENTS

| | | |
|---|---|---|
| CN | 104777419 A | 7/2015 |
| CN | 105492068 A | 4/2016 |
| CN | 105829903 A | 8/2016 |
| EP | 0 972 540 A2 | 1/2000 |
| EP | 2 216 072 A1 | 8/2010 |
| EP | 2 338 544 A1 | 6/2011 |
| EP | 2 338 545 A1 | 6/2011 |
| FR | 2 537 727 A1 | 6/1984 |
| JP | S 61-500893 A | 5/1986 |
| JP | S62-501190 A | 5/1987 |
| JP | H08-62663 A | 3/1996 |
| JP | 2006-61178 A | 3/2006 |
| JP | 2006-153819 A | 6/2006 |
| JP | 2007-003230 A | 1/2007 |
| JP | 2013-236475 A | 11/2013 |
| JP | 2016-509708 A | 3/2016 |
| JP | 2017-080500 A | 5/2017 |
| WO | WO 2012/022539 A1 | 2/2012 |
| WO | WO 2014/100557 A2 | 6/2014 |

OTHER PUBLICATIONS

Yang et al., Analysis of Influence of Internal Resistance of Lithium Battery and Group Connection thereof on Battery Management System, Measurement & Control Technology, 2014, vol. 12, pp. 147-150.

Xu et al., Lithium Battery Remote Monitoring System for Vehicle Mounted, 2017 29th Chinese Control And Decision Conference (CCDC), 2017, pp. 6895-6900.

* cited by examiner

MEDICAL DEVICE WITH POWER-UP ROUTINE

RELATED APPLICATIONS

This application is a continuation of PCT/EP2019/082796, filed Nov. 27, 2019, which claims priority to EP 18 209 404.5, filed Nov. 30, 2018, the entire disclosures of both of which are hereby incorporated herein by reference.

BACKGROUND

This disclosure relates to battery powered medical devices, such as extracorporeal insulin pumps as well as methods for powering up such battery-powered medical devices. The method especially relates to testing a battery in the powering up.

Battery-powered medical devices are used in large and increasing numbers in several diagnostic and therapeutic applications. A field to which reference is made in the following for exemplary purposes are extracorporeal insulin pumps that are carried by a Person with Diabetes (PwD) substantially continuously in the context of Continuous Subcutaneous Insulin Infusion (CSII).

Such extracorporeal insulin pumps and a variety of other medical devices are powered by a general-purpose battery that is removably arranged in a corresponding battery compartment of the medical device. When empty, the battery is typically replaced directly by the user.

Battery-powered medical devices are typically designed to monitor the battery and provide an alarm or alert to the user when the battery charge approaches depletion and the battery needs to be replaced. Further, it is common for battery-powered medical devices to carry out battery tests as part of a powering-up routine after replacing the battery. Thereby, it is ensured that the newly inserted battery is in fact capable of powering the medical device. For testing the battery of a medical device, a number of approaches have been developed and generally depend on voltage and internal resistance measurements.

Executing battery tests according to the prior art, however, are generally associated with a substantial stress to the battery, which may result in an unexpected power breakdown. This may especially occur if a generally unsuited battery is used, or if a weak or substantially depleted battery is mistakenly used instead of a fresh battery. If such power breakdown occurs when powering up the medical device, the medical device may completely stop operation without providing any warning or alarm to the user, which is known to be a reason of concern and worry for some users. Further, no information regarding the battery test is in this case stored in the history memory or history file of the medical device, thereby complicating the diagnostics of the power breakdown reason and further being critical from a regulatory point of view.

SUMMARY

This disclosure improves the state of the art regarding battery tests of a battery-powered medical device. Favorably, the risk of unexpected power breakdowns due to a weak or depleted battery can be avoided or at least reduced, according to these teachings.

A method for powering up a medical device powered by a battery includes executing an initial battery test. The initial battery test including the steps of:

a) determining a no-test-load voltage $U_{NoTestLoad}$ of the battery without a test load being connected to the battery;

b) providing an alarm if the no-test-load voltage $U_{NoTestLoad}$ is below a predetermined no-test-load voltage threshold $U_{Threshold,NoTestLoad}$ and terminating the method;

c) if the no-test-load voltage $U_{NoTestLoad}$ is above the no-test-load voltage threshold $U_{Threshold,NoTestLoad}$ executing the steps of:

c1) determining a test-load voltage $U_{TestLoad}$ of the battery with a test load being connected to the battery;

c2) comparing a difference voltage $\Delta U$ between the no-test-load voltage $U_{NoTestLoad}$ and the test-load voltage $U_{TestLoad}$ with a difference voltage threshold $\Delta U_{Threshold}$, the difference voltage threshold $\Delta U_{Threshold}$ being predefined in dependence of the no-test-load voltage $U_{NoTestLoad}$;

c3) if the difference voltage $\Delta U$ is above the difference voltage threshold $\Delta U_{Threshold}$, providing an alarm;

wherein the method further includes executing subsequent steps of the method if the difference voltage $\Delta U$ is below the difference voltage threshold $\Delta U_{Threshold}$.

A battery-powered medical device may include:—
  a battery compartment, the battery compartment being designed to removably hold a battery and contact elements for electrically contacting the battery;
  a test load, the test load being selectively coupleable to the battery;
  a control circuit (or controller), the control circuit being configured to execute a method for powering up the medical device upon a battery being inserted into the battery compartment.

The method for powering up the medical device may be a method according to any embodiment as described above and/or further below.

The battery generally be of any suited type. In typical embodiments, the battery is a generally available standard battery, such as for example, a AA or AAA cell of rechargeable or non-rechargeable type. The battery may also be made of a number of individual batteries in series. It is noted, however that the present invention is not limited to particular types of battery, but that an in principle any type of battery, being it a non-rechargeable battery (primary cell) or a rechargeable battery (secondary cell) may be used in accordance with the specifications and requirements of the medical device. The battery compartment is generally designed to allow battery replacement by a user.

Since the battery is contacted via contact elements of the battery compartment, the transition resistance between the contact elements and the battery terminals of the battery acts in series to the internal resistance of the battery as such. The combined resistance is in this document referred to as effective internal resistance $R_i$. In some typical embodiments, at least one of the contact elements is realized as a contact spring. In this document, the reference to the battery voltage generally refers to the terminal voltage that can be measured in the operational medical device, taking into account the voltage drop over the effective internal resistance $R_i$.

Subsequent steps of a method for powering up the medical device may include, for example, memory checks, communication controller checks, electrode checks, sensor checks, alarm checks, general checks of the medical device circuitry, tests of acoustic and/or tactile indication devices, such as loudspeakers buzzers or vibrators, display tests, and general initialization steps as generally known in the art as well as a further battery test as explained in more detail below. Some of these subsequent steps may be associated with a substantial power consumption and accordingly substantially stress the battery. In accordance with the present invention, these subsequent steps are only executed if the initial battery test is passed successfully.

It is to be understood that the medical device draws, when performing any operation and in particular when executing the initial battery test, a baseline current that cannot be avoided. As a consequence, the true open-circuit voltage $U_0$ of the battery is not available and cannot be measured, since the baseline current will in any case cause a voltage drop over the effective internal resistance. The baseline current is drawn by the control circuitry in operation. In the following, the baseline current during the initial battery test is generally assumed as constant.

When determining, in particular, measuring the no-test-load voltage in step (a), the baseline current is the only current that is drawn from the battery. Consequently, the battery load is minimum and the no-test-load voltage is as close as possible to the open-circuit voltage.

In step (b) of the method, an alarm is provided and the method is terminated, i.e., the subsequent steps are not executed, if the no-test-load voltage is below a predetermined no-test-load voltage threshold. This step ensures that the subsequent steps of the initial battery test are only executed if the battery is at least capable of providing the power that is required for such steps. Very weak or close-to-empty batteries are accordingly sorted out in this step. The alarm may be provided, like further alarms, on one or more indication devices of the medical device, indicated on a display of the medical device and/or provided on a remote device, such as a remote control or smart phone.

In step (c1), a further voltage of the battery is determined (measured) as test-load voltage with a test load being connected to the battery. Connecting and disconnecting the test load is controlled by the control circuit of the medical device. For this measurement, an additional test load current is drawn from the battery in addition to the baseline current, resulting in a larger voltage drop over the effective internal resistance.

The test load and the test load current are selected such that connecting the test load does not significantly stress the battery and may therefore be considered as "weak" test load. The test load current only needs to be sufficiently large to result in a safely measurable difference voltage between the no-test-load voltage and the test-load voltage.

In step (c2), the difference voltage $\Delta U$ between the no-test-load voltage $U_{NoTestLoad}$ as determined in step (b) and the test-load voltage as determined in step (c1) is compared with a difference voltage threshold. This difference voltage threshold is predefined in dependence of the no-test-load voltage. A relation between the difference voltage threshold $\Delta U_{Threshold}$ and the no-test-load voltage $U_{NoTestLoad}$ may be stored in a memory of the control circuit, for example, by way of a mathematical function or in form of a look-up table.

In dependence of the comparison result, an alarm is provided in step (c3) as explained before if the difference voltage is above the difference voltage threshold and the method terminates. Otherwise, the powering up is continued and completed by executing subsequent steps of the method. The subsequent steps of the method are accordingly only executed if the battery is capable of powering the medical device for the subsequent steps of the powering up routine without the risk of a sudden breakdown.

It is particularly noted that the initial battery test does not rely on an explicit impedance measurement and does further not require any demanding computational steps. What is required are only two voltage measurements and a subsequent threshold comparison. Therefore, it can be implemented in an efficient and straight-forward way. The determination of the difference voltage threshold in dependence of the no-test-load voltage is explained further below in more detail.

Overall, the initial battery test is a two-step test with a first step being defined by method steps (a), (b), and the second step being defined by method steps (c1), (c2), (c3).

In an embodiment, the difference voltage threshold is a linear function of the no-test-load voltage. This type of embodiment is particularly favorable with respect to a simple evaluation with very little computational effort.

In an embodiment, the test load is a constant resistance test load. In a non-limiting example that is typical, e.g., for some types of extracorporeal insulin pumps, the n-test-load voltage $U_{NoTestLoad}$ may be in a range of, e.g., 1.0V to 1.6V and a baseline current $I_B$ of ~500 µA may be typically used.

In an embodiment, the initial battery test includes storing a result of the initial battery test in a history memory of the medical device. The initial battery test in accordance with the present disclosure ensures that the battery, even if weak or close-to-empty, provides sufficient power for storing the result of the battery test prior to any full breakdown. Storing the result of the battery test is highly desirable for the purpose of device diagnostics and may further be a regulatory requirement. In a particular embodiment, the result is not stored in any case but only if a storing criterion is met that indicates that the battery may be weak. As a minimum, it may be stored whether or not the initial battery test as explained before is passed or failed. In further embodiments, the result may be stored for the first step of the initial battery test as defined by steps (a), (b) and the second step of the initial battery test as defined by steps (c1), (c2), (c3). Further, numerical values such as the no-test-load voltage and the test-load voltage may be stored and/or a binary test result (e.g., "passed" or "failed") may be stored.

In an embodiment, the method includes, if it is determined in step (c2) that the difference voltage $\Delta U$ is below the difference voltage threshold $\Delta U_{Threshold}$, executing a further battery test. The further battery test includes drawing a further test load current, thereby stressing the battery beyond a limit that is expected to occur during regular operation of the medical device.

In an embodiment the method may further include before step a):

0) turning on the power of the medical device.

The power may for example be turned on by activating a switch, by establishing a connection between the battery with a conductor of the medical device, such as by means of closing the battery compartment or by inserting the battery into the battery compartment, by connecting the battery to the battery contacts, etc. This preferably closes the circuitry of the battery with a processor of the medical device. Such switches are generally known to the skilled person and include buttons, transistors, induction switches, relays, etc.

In contrast to the initial battery test that is designed not to significantly stress the battery, the further battery test is a dedicated stress test which stresses the newly inserted battery to the limits of regular operation. By way of example for some types of extracorporeal insulin pumps, the further battery test may include drawing a battery current of ~1.0 A for 4 ms. The further battery test may, e.g., be considered as failed if the voltage at the end of the test falls below a predetermined threshold of, e.g., 985 mV.

In an embodiment, the battery-powered medical device includes one or more DC/DC step-up converter(s), the DC/DC step-up converter(s) powers at least some functional units of the medical device. In an example, the test load of such embodiment is electrically arranged between the battery contacts and an input side of the DC/DC step-up converter(s). Functional units that are powered via DC/DC step-up converter(s) typically include the control circuit, in particular, microcontrollers or processors, one or more indication devices or displays as explained before, actuators such as a motor in case of an infusion pump, communication interfaces, and the like. Typically, most of the functional components and circuitry of the medical device is powered via DC/DC step-up converter(s). For operation of the medical device, it must be ensured that at any point in time required minimum input voltage at the input side of the side of the DC/DC step-up converter is not fallen below. This requirement also holds true for the initial battery test. In some alternative embodiments, however, the test load is arranged on the output side of a DC/DC step-up converter.

In an embodiment, the control circuit comprises a processor or computer and a computer readable storage medium, the computer-readable storage medium comprising instructions which, when executed by the processor or computer cause the processor or computer to control execution the method for powering up the medical device. In an embodiment with DC/DC step-up converter(s) as explained before, the processor or computer is typically powered via a DC/DC step-up converter.

In an embodiment, the medical device is an extracorporeal insulin pump, the extracorporeal insulin pump being configured to be carried by a user for an extended time period under clothing and/or attached to the body.

In an embodiment the present disclosure is applicable to and useful for a variety of battery-powered devices including any battery-powered medical device including but not limited to a drug infusion pump including an insulin pump, a blood glucose sensor, a continuous glucose sensor, a heart defibrillator, a heart monitoring device, etc. Extracorporeal insulin pumps, however, are particularly critical since their failure may directly result in severe medical complications and they need to be operable substantially continuously around the clock. Further, they are frequently powered by ordinary general-purpose batteries, such as, for example rechargeable or non-rechargeable AA or AAA cells, and it is known that generally unsuited and/or almost empty batteries are occasionally used or reused by mistake and/or lack of awareness. Under such circumstances, a breakdown of the power supply as explained before is likely to occur during the process of powering up.

As known in the art, an insulin pump is designed for the administration of small liquid quantities in the microliter or sub microliter range with high precision. Further, insulin pumps are generally designed to administer drug substantially continuously according to a time-varying basal infusion profile and further administer larger drug amounts on demand.

A method for determining the difference voltage threshold $\Delta U_{Threshold}$ in dependence of the no-test-load voltage $U_{NoTestLoad}$ for use in a method as described above includes t the steps of:
 (1) experimentally determining a functional relation between values of an effective internal resistance $R_i$ and values of an open-circuit voltage $U_0$ for which the battery is capable of powering-up the medical device;
 (2) determining a minimum no-test-load voltage $U_{NoTestLoad,min}$ of the battery for powering up the medical device without a test load being connected to the battery as a function of the open-circuit voltage $U_0$ based on the functional relation as determined in step (1);
 (3) determining a minimum test-load voltage $U_{TestLoad,min}$ of the battery for powering up the medical device with a test load being connected to the battery as a function of the open-circuit voltage $U_0$ based on the functional relation as determined in step (1);
 (4) computing the difference voltage threshold $\Delta U_{Threshold}$ from the difference between the minimum no-test-load voltage $\Delta U_{NoTestLoad}$,min and the minimum test-load voltage $U_{TestLoad,min}$ in dependence of the minimum no-test-load voltage $U_{NoTestLoad}$,min with the open circuit voltage $U_0$ as parameter.

In an embodiment, the method includes determining the functional relation between values of the effective internal resistance $R_i$ and values of the open-circuit voltage $U_0$ as approximated linear functional relation.

In an embodiment, the method includes computing the difference voltage threshold $\Delta U_{Threshold}$ as linear approximation.

It is noted that the method for determining the difference voltage threshold $\Delta U_{Threshold}$ does not need to be implemented in the battery-powered medical device. Only the determined difference voltage threshold $\Delta U_{Threshold}$ in dependence of the minimum no-test-load voltage $U_{NoTestLoad,min}$ is stored in the medical device.

Instead, the method for determining the difference voltage threshold $\Delta U_{Threshold}$ in dependence of the no-test-load voltage $U_{NoTestLoad}$ is carried out by a medical device supplier in its facilities. Here, the open-circuit voltage $U_0$ and the effective internal resistance $R_i$ can be measured.

Further explanations and aspects regarding this aspect of this disclosure are provided in more detail below in the context of exemplary embodiment.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
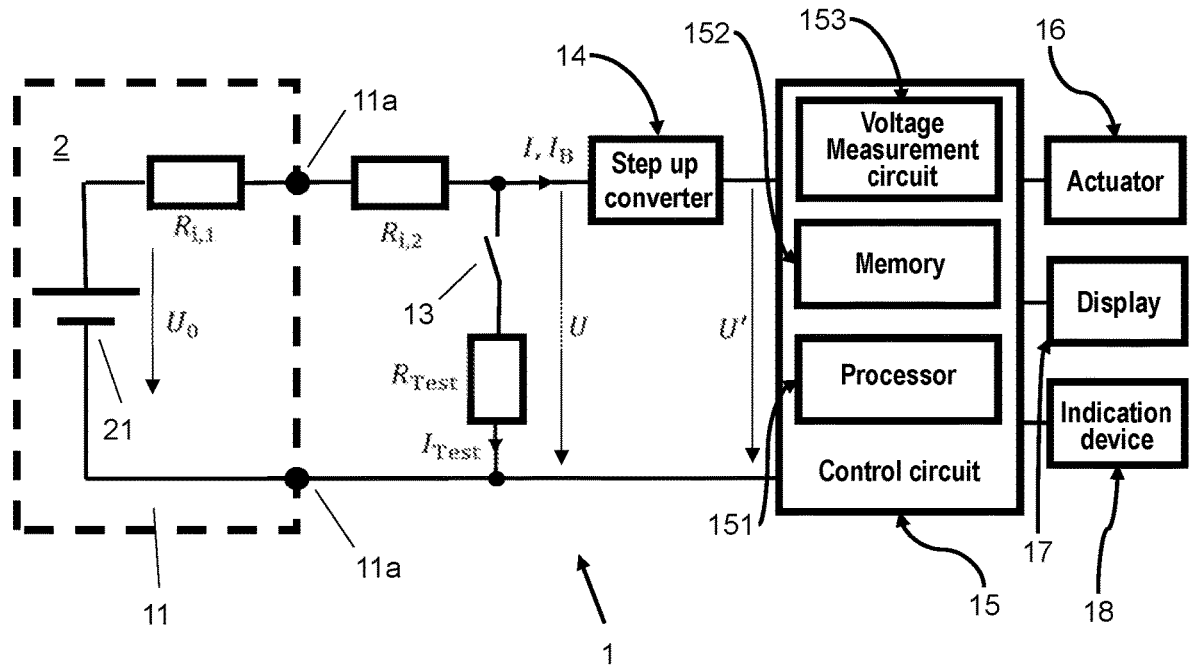
FIG. 1 schematically shows an exemplary battery-powered medical device with a battery.

FIG. 1 shows a battery-powered medical device 1 which is exemplarily an insulin pump together with a battery 2 in a schematic functional view. The battery 2 is removably arranged inside a battery compartment 11 of the medical device 1. Further, the battery 2, for example a rechargeable or non-rechargeable AA cell or AAA cell, is modelled as ideal battery 21 with open-circuit voltage $U_0$ and an internal resistance $R_{i,1}$. The battery 2 is contacted and connected with the further components of the medical device 1 via battery contacts 11a. The battery contacts 11a have a transition resistance $R_{i,2}$ in series with the internal resistance $R_{i,1}$ of the battery 2. In combination, the internal resistance $R_{i,1}$ of the battery 2 and the transition resistance $R_{i,2}$ form the effective internal resistance $R_i$. The terminal voltage of the battery 2 is referred to as U.

The medical device 1 further includes a DC/DC step-up converter 14 that is connected to the battery contacts 11a. The medical device 1 further includes a control circuit 15 that is connected to the output side of the DC/DC step-up converter. The control circuit 15 as well as further components as explained below are accordingly powered from the battery 2 via the DC/DC step-up converter 14.

The control circuit 15 includes a processor 151 with corresponding software in particular firmware code, memory 152 and a voltage measurement circuit 153 for measuring the terminal voltage U of the battery 2. Memory 151 may include both program storage that stores firmware code for processor 151 as well as Random Access Memory RAM as data memory. Further, control circuit 15 controls opening and closing of switch 13. Via switch 13, a constant resistance test load $R_{Test}$ test load that is implemented as can be connected to the battery in parallel to the contact elements 11a.

The current that is drawn by the test load $R_{Test}$ if switch 13 is closed is the test load current $I_{Test}$. The current I that is drawn by the medical device 1 apart from the test load current $I_{Test}$ is referred to as I. During an initial battery test as explained further below, it is the baseline current $I_B$.

Processor 151, memory 152, and voltage measurement circuit 153 may also be integrated, e.g., in form of a microcontroller as core element of control circuit 15. The control circuit 15 may and typically does further comprise a variety of further components and functional units as generally known in the art.

The battery-powered medical device 1 in the form of an extracorporeal insulin further includes an actuator 16 in form of an electric motor, a display 17 and at least one acoustic and/or tactile indication device 18, all of which operate under control of the control circuit 15.

It is noted that the design as shown in FIG. 1 is schematic and simplified for the sake of clarity and conciseness and in order to focus on aspects of particular relevance in the context of this disclosure. By way of example, more than one DC/DC step-up converters may be present that supply different functional components shown DC/DC step-up converter may be omitted. Further, the test load $R_{Test}$ may be arranged on the output side of the DC/DC step-up converter 14. Further, the test load $R_{Test}$ is not necessarily realized by a standard constant resistor, but may be realized by other circuitry such as a FET to form a controlled resistor.

Figure 2:
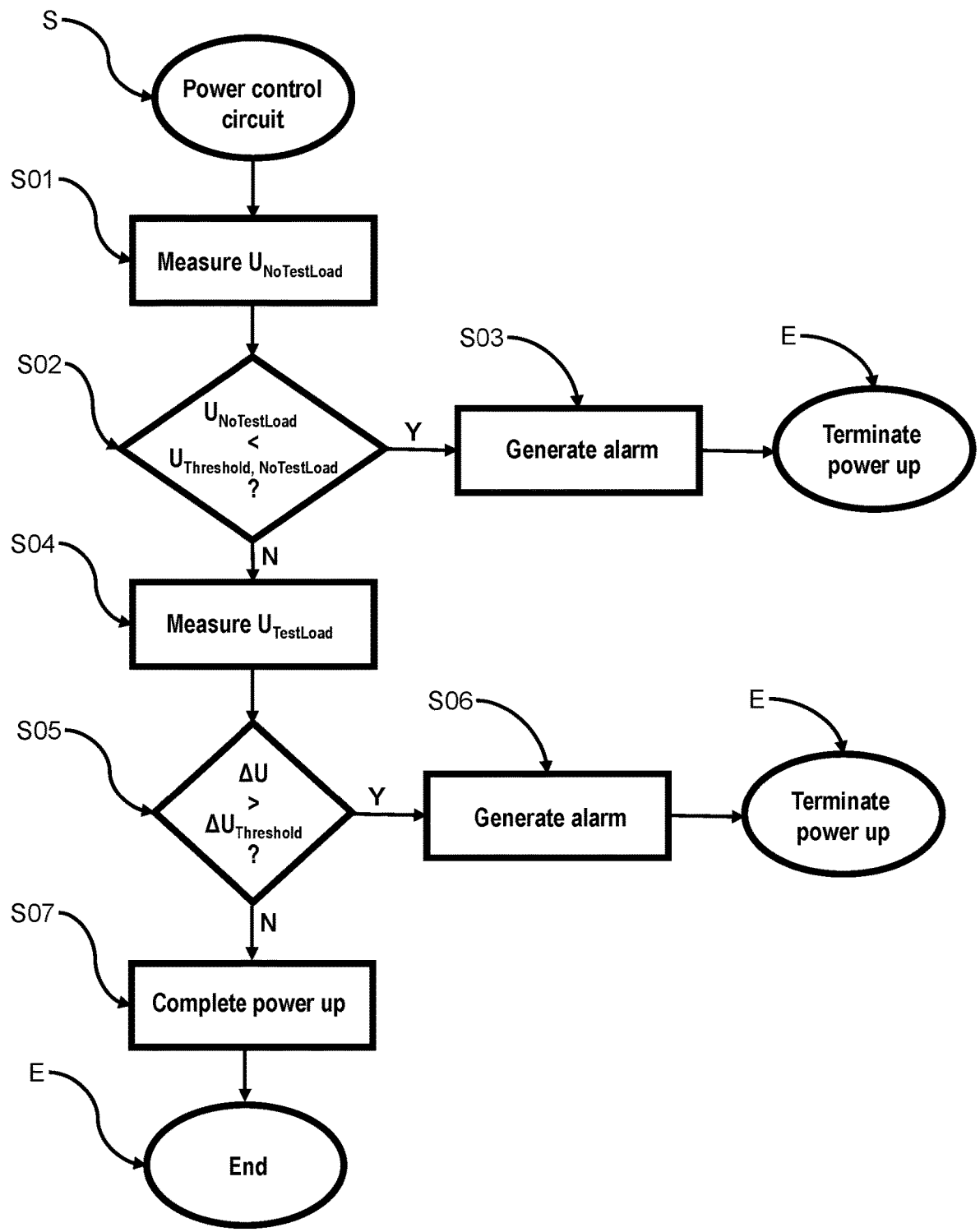
FIG. 2 shows an exemplary operational flow for powering up a medical device.

The control circuit 15 implements a method for powering up the medical device 1, which is explained in more detail with additional reference to FIG. 2. The operational flow starts in step S where battery 2 is placed into the battery compartment 11, resulting in the medical device 1 and in particular the control circuit 15 being supplied with power. In step S01, the voltage U is measured via the voltage measurement circuit 153. In this state, the switch 13 is open, and the measured voltage is accordingly the no-test-load voltage, $U=U_{NoTestLoad}$, with $I=I_B$ as baseline current.

In subsequent step S02, the no-test-load voltage $U_{NoTestLoad}$ is compared with a no-test-load voltage threshold $U_{Threshold,NoTestLoad}$ that is stored in memory 152 and the operational flow branches in dependence of the result. If the no-test-load voltage $U_{NoTestLoad}$ is below the no-test-load voltage threshold $U_{Threshold,NoTestLoad}$, the operational flow proceeds with step S03. In Step S03 an alarm is generated and indicated via display 17 and indication devices 18. Further, a corresponding entry is written into a history memory which is part of memory 152. Subsequently, the operational flow ends with step E and the powering up is terminated. The alarm may be indicated until the battery 2 is fully emptied respectively removed. In an exemplary realization where the battery 2 is an ordinary, commercially available standard cell and the no-test-load voltage threshold $U_{Threshold,NoTestLoad}$ may be, for example 1000 mV respectively 1 V.

If it is determined in step S02 that the no-test-load voltage $U_{NoTestLoad}$ is above the no-test-load voltage threshold $U_{Threshold,NoTestLoad}$, the operational flow proceeds with step S04. In step S04, the voltage U is measured via the voltage measurement circuit 153 with switch 13 being temporarily closed. The measured voltage is accordingly the test-load voltage, $U=U_{TestLoad}$, and the current that is drawn from the battery 2 corresponds to the sum of the baseline current $I_B$ and the test current $I_{Test}$.

In subsequent step S05, the difference voltage $\Delta U=U_{NoTestLoad}-U_{TestLoad}$ is determined and compared with a difference voltage threshold $\Delta U_{Threshold}$ which is predefined in dependence of the no-test-load voltage $U_{NoTestLoad}$. The relation between the difference voltage threshold $\Delta U_{Threshold}$ and the no-test-load voltage $U_{NoTestLoad}$ may be stored in and retrieved from memory 152 in form of a look-up table or may be provided in form of an equation $\Delta U_{Threshold}=f(U_{NoTestLoad})$ which may especially be a linear equation and is evaluated by control circuit 15, in particular processor 151. This aspect is also discussed further below.

If it is determined in step S05 that the difference voltage $\Delta U$ is above the difference voltage threshold $\Delta U_{Threshold}$, the operational flow proceeds with step S06. In Step S06 an alarm is generated and indicated as explained before in the context of step S03 and a corresponding entry is again written into the history memory. Also like in step S03, the operational flow ends with step E and the powering up is terminated.

If it is determined in step S05 that the difference voltage $\Delta U$ is below the difference voltage threshold $\Delta U_{Threshold}$, the operational flow proceeds with step S07 where the powering up is continued and completed. Step S07 may include executing a further battery test as explained before in the general description.

In the following, the functional relation between the difference voltage threshold $\Delta U_{Threshold}$ and the no-test-load voltage $U_{NoTestLoad}$ is discussed in more detail.

In investigating the start-up behavior of a battery-powered medical device and in particular an extracorporeal insulin pump as explained before, it is found that correct start-up is in any case possible if the effective internal resistance $R_i$ meets the condition $$R_i < r_i(U_0)=k_1 \cdot U_0+k_2 \tag{1a}$$

Consequently, for the effective internal resistance $R_i$ being given, the open-circuit voltage $U_0$ needs to meet the condition $$U_0 > u_0(R_i) = \frac{R_i - k_2}{k1}. \tag{1b}$$

Further, it can be seen from FIG. 1 that the following applies:

$$U_0 = R_i \cdot I_B + U_{NoTestLoad}, \quad (2a)$$

$$U_0 = R_i \cdot \left(I_B + \frac{U_{TestLoad}}{R_{Test}}\right) I_B + U_{NoTestLoad}, \quad (2b)$$

with Eqn. (2a) applying during the initial battery test with switch 13 being open and Eqn. (2b) applying during the initial battery test with switch 13 being closed.

In the following, a voltage on the output side of the DC/DC step-up converter 14 (i.e., the supply voltage of control circuit 15) is referred to as U'. Further, the (virtual) load resistance that is seen by the battery 2 as drawing the baseline current $I_B$ is referred to as $R_B$. Eqn. (2a), (2b) can accordingly be re-written as $$U_0 = \frac{R_i}{R_B} \cdot \frac{U'^2}{U_{NoTestLoad}} + U_{NoTestLoad}, \quad (3a)$$

$$U_0 = \frac{R_i}{R_B} \cdot \frac{U'^2}{U_{TestLoad}} + \left(\frac{R_i}{R_{Test}} + 1\right) \cdot U_{TestLoad}. \quad (3b)$$

By re-arranging Eqn. (3a), (3b) for $U_{NoTestLoad}$ and $U_{TestLoad}$, respectively and solving the resulting quadratic equations, the following is obtained:

$$U_{NoTestLoad}(U_0, R_i) = \frac{U_0}{2} + \sqrt{\left(\frac{U_0}{2}\right)^2 - \frac{R_i}{R_B} \cdot U'^2} \quad (4a)$$

$$U_{TestLoad}(U_0, R_i) = \quad (4b)$$

$$\frac{U_0}{2} \cdot \frac{R_{Test}}{R_{Test} + R_i} + \sqrt{\left(\frac{R_{Test}}{R_{Test} + R_i} \cdot \frac{U_0}{2}\right)^2 - \frac{R_{Test}}{R_{Test} + R_i} \cdot \frac{R_i}{R_B} \cdot U'^2}.$$

Eqn. (4a, 4b) accordingly express the voltages $U_{NoTestLoad}$, $U_{TestLoad}$ for the battery 2 that can be measured in the medical device 1 in operation as function of the generally unknown open-circuit voltage $U_0$ and effective internal resistance $R_i$.

In Eqn. (4a, 4b), the effective internal resistance may be substituted by its threshold value for which a powering-up is possible according to Eqn. (1a), resulting in equations for the minimum no-test-load voltage $U_{NoTestLoad,min}$ and the minimum test load voltage $U_{TestLoad,min}$ with the open-circuit voltage $U_0$ as sole parameter.

Figure 3:
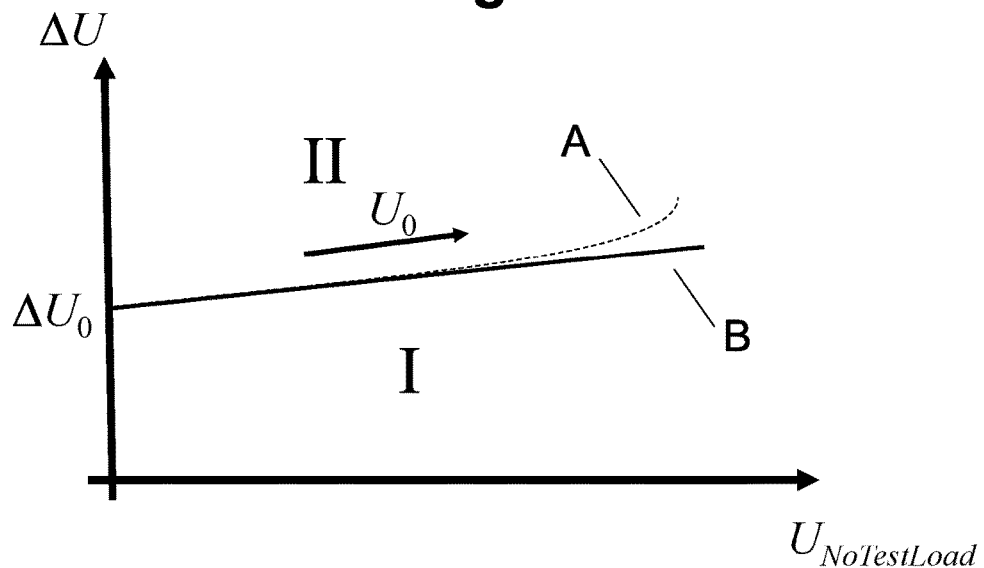
FIG. 3 shows exemplary graphs for a threshold difference voltage in dependence of a no-test-load voltage.

The graph of FIG. 3 schematically shows the difference voltage $\Delta U = U_{NoTestLoad} - U_{TestLoad}$ when plotted over the no-test-load voltage $U_{NoTestLoad}$ with the open-circuit voltage $U_0$ as parameter. Curve A is obtained from directly applying Eqn. (4a), (4b). In a region II above curve, a powering up the medical device 1 is not possible, while in the area I below the curve, powering up is possible. Curve A accordingly defines the difference voltage threshold $\Delta U_{Threshold}$ as a function respectively in dependence of the no-test-load voltage $U_{NoTestLoad}$ Curve A may be implemented in the control circuit 151 by way of a mathematical function that is evaluated by the processor 151 or may be implemented as look-up table in the memory 152.

A further computational simplification as explained in the following may be used in a further embodiment. Instead of curve A, the linear approximation of curve B is used. Curve B may be obtained as tangent to curve A at a reference value $\Delta U_0$. Like curve A, Curve B may be implemented in the control circuit 151 by way of a (linear) mathematical function that is evaluated by the processor 151 or may be implemented as look-up table in the memory 152. In an exemplary implementation, the reference value may be in the range of 1 mV.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF DESIGNATIONS 1 battery-powered medical device/extracorporeal insulin pump
11 battery compartment
11a contact element
13 switch
14 DC/DC step-up converter
15 control circuit
151 processor
152 memory
153 voltage measurement circuit
16 actuator/motor
17 display
18 indication device
2 battery
21 ideal battery
$U_0$ open-circuit voltage
U terminal voltage
U' voltage at output side of step-up converter
$R_{i,1}$ internal resistance of battery
$R_{i,2}$ transition resistance of contact elements
$R_{Test}$ test load resistance
$R_B$ virtual resistance drawing baseline current
$\Delta U$ difference voltage
$\Delta U_0$ reference value for difference voltage
$U_{NoTestLoad}$ no-test-load voltage
$U_{TestLoad}$ test-load voltage
$U_{Threshold,NoTestLoad}$ threshold voltage without test load
$\Delta U_{Threshold}$ difference voltage threshold
I current
$I_B$ baseline current
$I_{Test}$ test load current
$k_1$, $k_1$ constants
A, B curves

What is claimed is:

1. A method for powering up a medical device powered by a battery, comprising:
   a) determining a no-test-load voltage ($U_{NoTestLoad}$) of the battery without a test load ($R_{Test}$) being connected to the battery;
   b) providing an alarm when the $U_{NoTestLoad}$ is below a predetermined no-test-load voltage threshold ($U_{Threshold,NoTestLoad}$) and terminating the method;
   c) when the $U_{NoTestLoad}$ is above the $U_{Threshold,NoTestLoad}$ executing the steps of:
      c1) determining a test-load voltage ($U_{TestLoad}$) of the battery with the $R_{Test}$ being connected to the battery;
      c2) comparing a difference voltage ($\Delta U$) between the $U_{NoTestLoad}$ and the $U_{TestLoad}$ with a difference voltage threshold ($\Delta U_{Threshold}$), the $\Delta U_{Threshold}$ being predefined in dependence of the $U_{NoTestLoad}$;

c3) when the $\Delta U$ is above the $\Delta U_{Threshold}$, providing an alarm; and d) when $\Delta U$ is below $\Delta U_{Threshold}$, completing the powering up of the medical device.

2. The method according to claim 1, wherein the $\Delta U_{Threshold}$ is a linear function of the $U_{NoTestLoad}$.

3. The method according to claim 1, wherein the $R_{Test}$ is a constant resistance test load.

4. The method according to claim 1, wherein the initial battery test includes storing a result of the initial battery test in a history memory of the medical device.

5. The method according to claim 1, wherein, when it is determined in step (c2) that the $\Delta U$ is below the $\Delta U_{Threshold}$, executing a further battery test, wherein the further battery test includes drawing a further test load current, thereby stressing the battery to a limit that is expected to occur during regular operation of the medical device and providing an alarm if it is determined that the battery is not capable of powering the medical device.

6. The method according to claim 1, wherein the method includes before step a), turning on the power of the medical device.

7. The method according to claim 1, wherein the subsequent steps include at least one of the following: memory checks, communication controller checks, medical device circuitry checks, sensor checks, electrode checks, checking of a communication controller, tests of acoustic indication devices, checks of tactile indication devices, and initializing steps of the medical device.

8. A battery-powered medical device, comprising:
a battery compartment configured to removably hold a battery and contact elements for electrically contacting the battery;
a test load ($R_{Test}$) selectively coupleable to the battery; and
a control circuit configured to execute the method according to claim 1.

9. The battery-powered medical device according to claim 8, further comprising one or more DC/DC step-up converters powering at least some functional units of the medical device, wherein the $R_{Test}$ is electrically arranged between the contact elements and an input side of the DC/DC step-up converter.

10. The battery-powered medical device according to claim 8, wherein a relation between the $\Delta U_{Threshold}$ and the $U_{NoTestLoad}$ is stored in a memory of the control circuit.

11. The battery-powered medical device according to claim 8, wherein the medical device is an extracorporeal insulin pump configured to be carried by a user for an extended time period under clothing and/or attached to the body.

12. The method according to claim 1, further comprising:
(1) experimentally determining a functional relation between values of an effective internal resistance ($R_i$) and values of an open-circuit voltage ($U_0$) for which the battery is capable of powering-up the medical device;
(2) determining a minimum no-test-load voltage ($U_{NoTestLoad,min}$) of the battery for powering up the medical device without the $R_{Test}$ being connected to the battery as a function of the open-circuit voltage $U_0$ based on the functional relation determined in step (1);
(3) determining a minimum test-load voltage ($U_{TestLoad,min}$) of the battery for powering up the medical device (1) with the $R_{Test}$ being connected to the battery as a function of the open-circuit voltage $U_0$ based on the functional relation as determined in step (1);
(4) computing the $\Delta U_{Threshold}$ from the difference between the $U_{NoTestLoad,min}$ and the $U_{TestLoad,min}$ in dependence of the $U_{NoTestLoad,min}$ with the $U_0$ as parameter.

13. The method according to claim 12, including determining the functional relation between values of the $R_i$ and values of the $U_0$ as an approximated linear functional relation.

14. The method according to claim 12, including computing the $\Delta U_{Threshold}$ as a linear approximation.

* * * * *